United States Patent [19]
Poirier

[11] Patent Number: 6,050,975
[45] Date of Patent: Apr. 18, 2000

[54] CONTROL OF TISSUE GROWTH IN TEXTURED BLOOD-CONTACTING SURFACES

[75] Inventor: Victor L. Poirier, Concord, Mass.

[73] Assignee: Thermo Cardiosystems, Inc., Woburn, Mass.

[21] Appl. No.: 09/257,021

[22] Filed: Feb. 25, 1999

[51] Int. Cl.[7] .................................................. A61M 37/00
[52] U.S. Cl. ........................ 604/131; 604/151; 604/500
[58] Field of Search .............................. 604/131, 93, 150, 604/151, 174, 175, 500

[56] References Cited

U.S. PATENT DOCUMENTS

| 4,446,229 | 5/1984 | Indech ........................................ 435/1 |
| 4,627,836 | 12/1986 | MacGregor ................................ 604/93 |
| 4,944,722 | 7/1990 | Carriker et al. ........................... 600/16 |
| 5,211,546 | 5/1993 | Isaacson et al. .......................... 417/356 |
| 5,632,779 | 5/1997 | Davidson ................................... 623/12 |

OTHER PUBLICATIONS

Parnis et al.; "Progress in the Development of a Transcutaneously Powered Axial Flow Blood Pump Ventricular Assist System"; Asaio J 43(5); Sep. 1997; pp. M576–M580.

MacGregor et al.; "The Porous–surfaced electrode"; The Journal of Thoracic and Cardiovascular Surgery 78(2); Aug. 1979; pp. 281–291.

MacGregor et al.; "Improved Thromboresistance of Mechanical Heart Valves with Endothelialization of Porous Metal Surfaces"; Surgical Forum 30; 1979; pp. 239–241.

Bobyn et al.; "Effect of pore size in the peel strength of attachment of fibrous tissue to porous–surfaced implants"; Journal of Biomedical Materials Research 16(5); Sep. 1982; pp. 571–584.

*Primary Examiner*—John D. Yasko
*Attorney, Agent, or Firm*—Fish & Richardson P.c.

[57] ABSTRACT

A blood pump provides a mechanism to prevent excessive growth of tissue at the transition zone between a smooth blood contacting surface and a textured blood contacting surface. The blood pump includes a blood flow channel having a textured surface, a smooth surface adjacent to the textured surface, and a rotor positioned within the blood flow channel. The rotor includes at least one impeller blade that defines a sweep when the rotor turns. The impeller blade is designed to cut off a portion of a biologic lining as it grows from the textured surface into the sweep of the impeller blade.

26 Claims, 11 Drawing Sheets

CONTROL OF TISSUE GROWTH IN TEXTURED BLOOD-CONTACTING SURFACES

TECHNICAL FIELD

The invention relates to blood contacting surfaces and, more particularly, to blood contacting surfaces in blood pumps.

BACKGROUND OF THE INVENTION

A number of implantable blood pumps are in use or under development for application as either artificial hearts or cardiac assist devices. Some of the blood pumps circulate blood based on rotary flow. A centrifugal flow pump, for example, causes blood to circulate by the turning of an impeller mechanism mounted on an axis in a blood flow chamber in which the axis is perpendicular to the direction of the blood flow. Another example of a blood pump is the axial flow pump, which causes blood to circulate by the turning of an impeller mechanism mounted within a blood flow chamber. The impeller mechanism rotates around an axis that runs in the direction of the blood flow. Both of these pumps may be implemented using a bearing system to maintain the position of the impeller mechanism. They also may be implemented using a magnetically levitated (i.e., bearingless) impeller mechanism mounted within a blood flow chamber.

The interior surface of the pump may be smooth or textured. A smooth surface is intended to prevent growth of a biologic lining of protein and cells, and may be used on moving parts in which a biologic lining is unlikely to form. Textured surfaces, on the other hand, are intended to prevent thromboembolic complications by promoting a biologic lining that adheres to the textured surface. A textured surface may be used on a stationary surface of a blood pump or on another surface not subject to high centrifugal or other forces that hinder or prevent adherence and growth of the lining.

SUMMARY OF THE INVENTION

The present invention is directed to a blood pump and to blood contacting surfaces such as interior surfaces of a blood pump. The pump incorporates one or more features capable of significantly improving the thrombogenic characteristics of the pump. If blood is in contact with a foreign surface there may be thromboembolic complications. If the blood is in contact with a natural endothelial surface or a surface having characteristics similar to an artery, the likelihood of thromboembolic complications may be reduced. One way to accomplish this goal is to use a textured blood contacting surface to induce the formation and adherence of a biologic lining derived from the blood that is in contact with the surface. At the junction between the textured and a smooth surface, however, the biologic lining is unlikely to adhere, or adhere strongly, to the smooth surface and a flap of tissue is formed. The tissue flap can become large, break off, and form an embolism, potentially causing a heart attack, stroke or other thromboembolic event. Thus, a mechanism to prevent the formation of a large tissue flap is desirable.

In one general aspect, a blood pump constructed according to the present invention provides a mechanism to prevent the growth of a large flap of tissue at the transition zone between a smooth and a textured surface. The blood pump includes a blood flow channel having a textured surface, a smooth surface adjacent to the textured surface, and a rotor disposed within the blood flow channel. The rotor includes an impeller blade that defines a sweep when the rotor turns and the impeller blade is configured to cut off a portion of a biologic lining as it grows from the textured surface into the sweep of the impeller blade.

Embodiments may include one or more of the following features. For example, the rotor may include multiple impeller blades or may be positioned adjacent to the smooth surface. The blood pump may be a rotary pump.

In one embodiment, the impeller blade may include a leading edge and the leading edge may be positioned adjacent to the smooth surface at a distance less than about 0.020 inches from the textured surface. In another embodiment, the distance may be between about 0.010 inches and about 0.015 inches.

The blood pump also may include a bearing mounted to the rotor, an inlet bearing block disposed in the blood flow channel, and at least one vane mounted to the bearing and defining a sweep of the vane when the rotor turns. The inlet bearing block may be configured to retain the bearing and have a textured surface configured to encourage the formation of a biologic lining. The vane may he configured to cut off a portion of the biologic lining growing from the textured surface of the inlet bearing block into the sweep of the vanes. The distance between the vane and the inlet bearing block may be less than about 0.020 inches. In another embodiment, the distance may be between about 0.010 and about 0.015 inches. The distance between the vane and the inlet bearing block is significant because that distance can limit the size of the biologic lining growing from the smooth surface.

The blood pump also may include an inlet bearing and an outlet bearing mounted on opposite ends of the rotor, an inlet bearing block configured to receive the inlet bearing, and an outlet bearing block configured to receive the outlet bearing. The blood pump also may include an inflow cannula pump adaptor, an inflow cannula elbow having a first end and a second end, and an inflow cannula apical tube connected to the second end of the inflow cannula elbow. The first end of the inflow cannula is connected to the inflow cannula pump adaptor.

Various surface may be textured. Any one or all of the inflow cannula pump adaptor, the inflow cannula elbow, and the outflow cannula elbow may have textured blood contacting surfaces. The inflow cannula apical tube may have a textured internal blood contacting surface and a textured external surface.

Another general aspect of the invention features a method for cutting a biologic lining on a blood contacting surface. The method includes providing a blood pump including a blood flow channel having a textured surface and an adjacent smooth surface, and positioning a rotor within the blood flow channel. The rotor has an impeller blade that defines a sweep when the rotor turns. The impeller blade is configured to cut off a portion of a biologic lining as it grows from the textured surface into the sweep of the impeller blade. The rotor may be positioned within the blood flow channel adjacent to the smooth surface.

In another general aspect, a blood pump includes a pumping housing and a pumping chamber having a collector region and a rotor disposed within the pumping chamber. The pumping chamber and the rotor define a narrow channel, the collector region has a textured blood contacting surface, and the rotor is configured to cut a biologic lining growing into the sweep of the rotor.

Embodiments may include one or more of the following features. For example, the narrow channel may have a textured blood contacting surface. The width of the narrow channel may be less than about 0.020 inches. Various blood contacting surfaces may be textured. For example, the rotor and the pumping chamber may have textured blood contacting surfaces. The rotor may include impeller blades, a shroud, and magnet base. The blood pump may be a centrifugal pump.

In another general aspect of the invention, an embolism-resistant device includes a textured blood contacting surface on which a biologic lining can grow, a smooth blood contacting surface adjacent to the textured surface, and a cutting means to cut a portion of the biologic lining as the biologic lining grows from the textured surface onto the smooth surface.

Embodiments may include one or more of the following features. For example, the cutting means may be positioned less than about 0.020 inches from the textured surface. The cutting means may be positioned between about 0.010 and about 0.015 inches from the textured surface. The embolism-resistant device may be a blood pump.

The rotor of the blood pumps described above may be maintained in a position within the pump by the use of bearings. Alternatively, the rotor may be magnetically levitated (i.e., a bearingless rotor) so that the rotor is maintained in a position by the use of magnetic forces.

Other features and advantages will be apparent from the following description, including the drawings, and from the claims.

DESCRIPTION OF THE PREFERRED EMBODIMENTS

Figure 1:
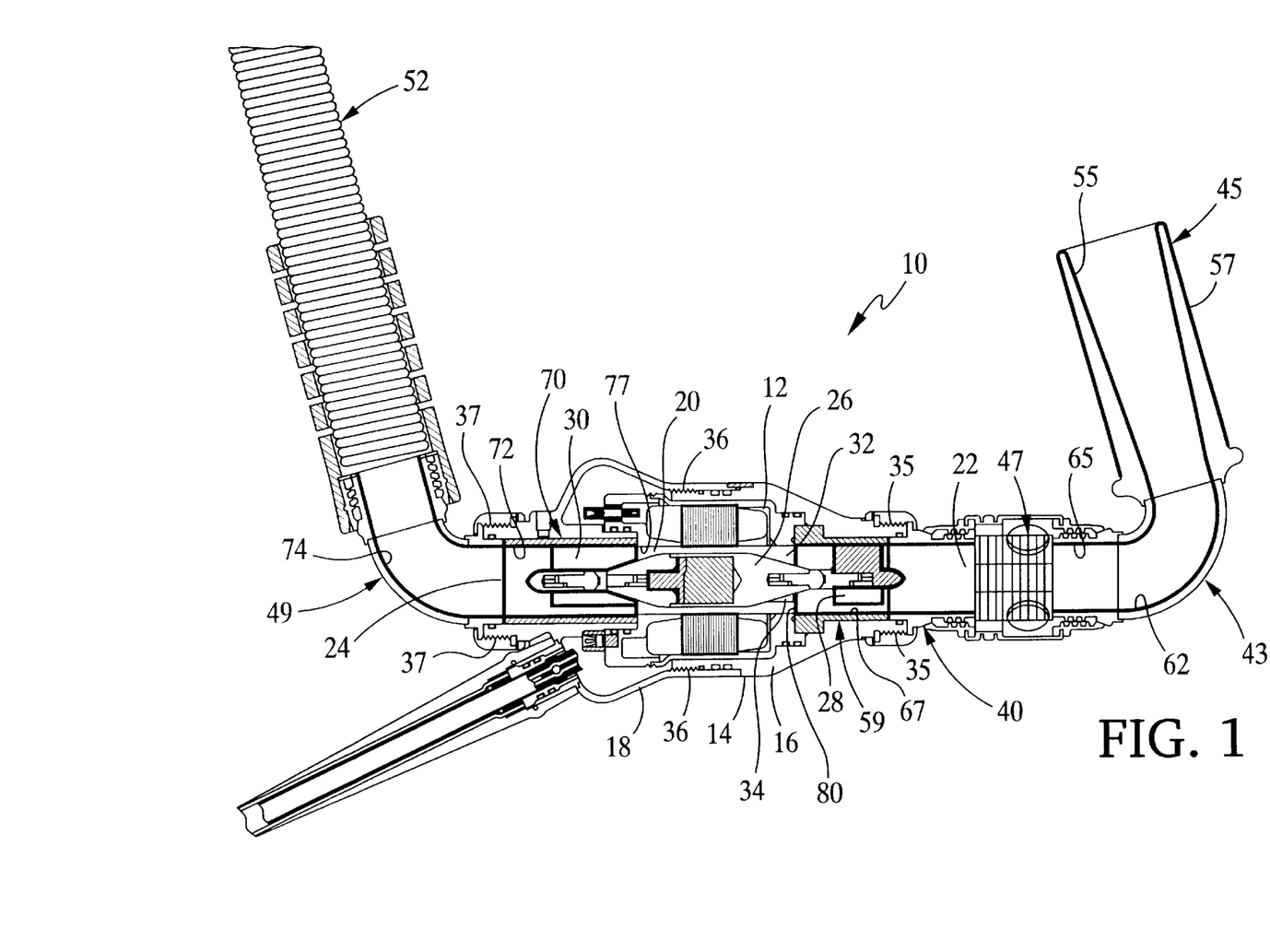
FIG. 1 is a cross-sectional view of an axial flow blood pump.

FIG. 1 is a longitudinal cross-sectional diagram of an implantable axial flow blood pump 10 incorporating a motor stator assembly 12. Blood pump 10 can be implanted within a human to provide the functions of an artificial heart or a cardiac assist device. As shown in FIG. 1, pump 10 includes a two-part pump housing 14 having an inflow portion 16 and an outflow portion 18. The interior of pump housing 10 defines a generally cylindrical blood flow channel 20. Inflow portion 16 has an inflow opening 22 through which blood enters flow channel 20. Outflow portion 18 has an outflow opening 24 through which blood exits flow channel 20. An elongated rotor 26 is disposed within pump housing 14 and extends axially along blood flow channel 20. Rotor 26 is mounted, at opposite ends, for rotation within inflow and outflow bearing blocks 28 and 30, respectively. Impeller blades 32 and 34 are mounted on rotor 26 and oriented to impart axial pumping energy to the blood flow upon actuation of the rotor. In FIG. 1, only two impeller blades 32 and 34 are visible. However, rotor 26 may carry three or more impeller blades, each arranged, for example, in a spiral-like pattern. Alternatively, rotor 26 may carry one impeller blade mounted in a screw-like pattern. Motor stator assembly 12 is disposed within pump housing 14 and is generally annular in shape.

With further reference to FIG. 1, inflow and outflow portions 16 and 18, respectively, of pump housing 14 are reciprocally threaded, as indicated by reference numeral 36, such that one can be screwed into the other to couple both portions and enclose motor stator assembly 12 and rotor 26. As indicated by reference numerals 35 and 37, inflow and outflow portions 16 and 18, respectively, also are threaded at opposite ends adjacent to inflow and outflow openings 22 and 24, respectively. Inflow portion 16 is threadably connected to an inflow cannula pump adaptor 40, which is connected to an inflow cannula elbow 43. Cannula elbow 43 is connected to an inflow cannula apical tube 45, which is inserted into the apex of the left ventricle (not shown). Inflow cannula pump adaptor 40 contains an inflow recovery graft 47.

Outflow portion 18 is threadably connected to an outflow cannula elbow 49, which is connected to an outflow graft 52. Outflow graft 52 is attached with sutures to the aorta (not shown) when the blood pump 10 is used as a cardiac assist device.

Various blood contacting surfaces of pump 10 may have a textured surface that encourages or promotes the formation and adherence of a biologic lining. The textured surfaces may be made from a metal, such as a powdered metal, or a polymer. For example, the textured surface may be a sintered titanium surface, such as that found in the Thermo Cardiosystems HeartMate®. Textured surfaces and their fabrication are known in the art and are used in a variety of medical applications.

For example, inflow cannula apical tube 45 has a textured internal surface 55 and a textured external surface 57. Both surfaces are textured because they are in contact with blood. The external surface 57 also is in contact with the tissue of the left ventricle. Thus, the textured surfaces 55 and 57 promote the growth and adherence of a biologic lining derived from blood and tissue.

Of the blood contacting surfaces upstream from the rotor 26, inflow cannula elbow 43, inflow cannula pump adaptor 40, and an inflow stator sleeve assembly 59 have textured internal surfaces 62, 65, and 67, respectively. Bearing block 28 may be smooth or textured. Inflow recovery graft 47 may be a polyester graft, which is inherently textured.

Of the blood contacting surfaces downstream from the rotor 26, outflow stator sleeve assembly 70 and outflow cannula elbow 49 have textured internal surfaces 72 and 74, respectively. Outflow graft 52 may be a polyester graft, which is inherently textured.

The blood contacting surfaces that are not textured include rotor 26, which includes impeller blades 32 and 34, and a blood tube surface 77 of blood flow channel 20 that is adjacent to rotor 26. Rotor 26 is not textured because the blood contacting surfaces of a fast moving component, such as rotor 26, are unlikely to be subjected to adherence of blood components if the velocity of the blood creates enough shear force to prevent adherence. In addition, the centrifugal force produced by the rotating rotor will also prevent cells from being adjacent to its surface. Similarly, a stationary surface subject to blood flowing past it at a high velocity, such as smooth blood tube surface 77, is unlikely to be subject to adherence of blood components because the shear forces of the blood flow will dislodge any adhered component when its size becomes large enough to impede flow. Additionally, anticoagulants taken by the recipient of the blood pump 10 reduce the tendency of blood to adhere to surfaces.

Because some of the blood contacting surfaces are textured and some are not, there are transitions zones between the textured and smooth surfaces. In the transition zones in which the direction of blood flow is from the textured surface to the smooth surface, such as from textured internal surface 67 to blood tube surface 77, the biologic lining formed on the textured surface will grow onto the smooth surface. In the transition zones in which the direction of blood flow is from the smooth surface to the textured surface, such as from blood tube surface 77 to textured internal surface 72, the biologic lining formed on the textured surface is less likely to grow onto the smooth surface because of the shear forces exerted by the blood flow in the direction away from the smooth surface.

Figure 2A:
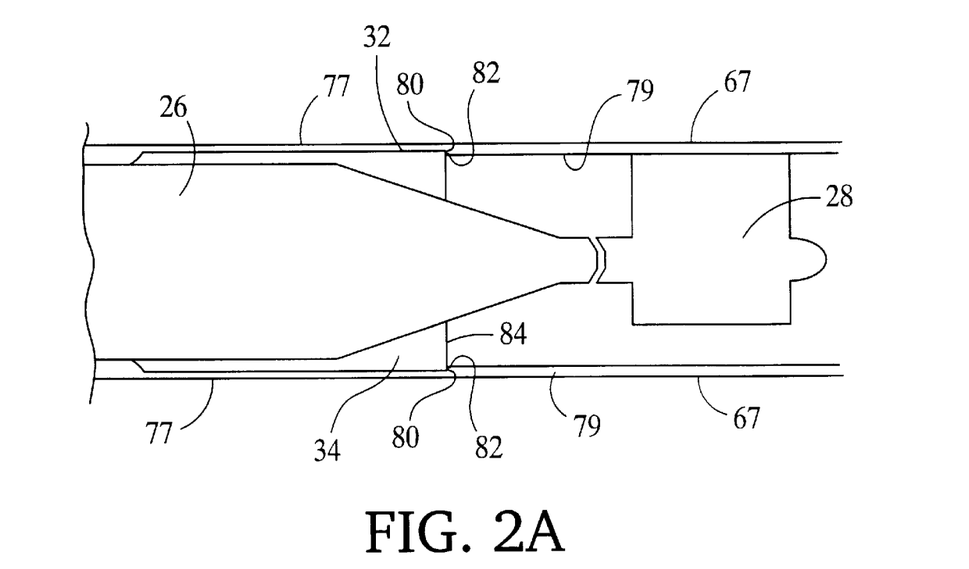
FIG. 2A is a cross-sectional view of a transition zone between a textured surface of an inflow stator sleeve assembly and a smooth blood tube surface of the axial flow blood pump of FIG. 1.
Figure 2B:
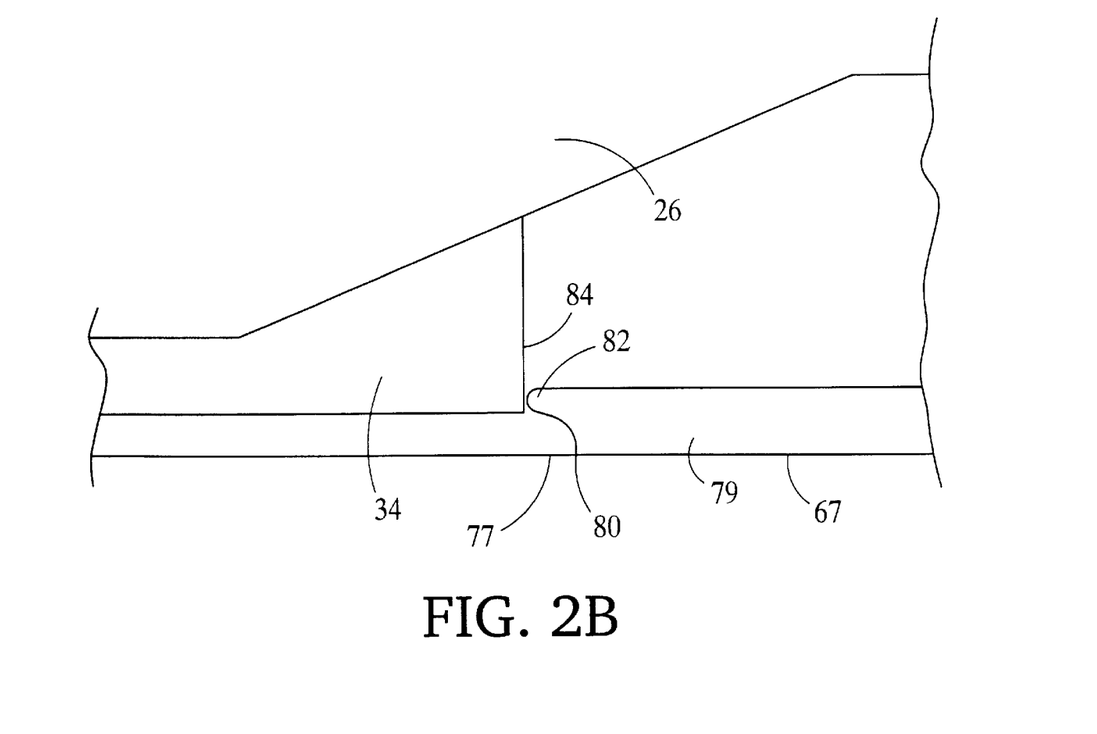
FIG. 2B is an enlarged cross-sectional view of the transition zone of FIG. 2A.

Referring to FIGS. 2A and 2B, a biologic lining 79 growing on textured surface 67 formed at a transition zone 80 between textured surface 67 and smooth blood tube surface 77 may grow a flap 82 that continues over smooth surface 77, but that may not have firm adherence or attachment. Growth of flap 82 beyond the transition zone 80 presents a concern because flap 82 will continue to proliferate from the textured surface 67, to which it can adhere, to the smooth surface 77, to which it cannot. As a result, flap 82 may become large, break off, and embolize in the blood stream, resulting in a clot lodging in a vessel causing a heart attack, stroke or other serious medical complication. The size of the tissue embolism can be on the order of one eighth of an inch.

To prevent such an event, a leading edge 84 of each impeller blades 32 and 34 is positioned so that a leading edge 84 is approximately 0.020 inches from the transition zone 80. The leading edge 84 may be sharpened or left blunt. If tighter tolerances on the components can be achieved, the inlet edge may be positioned between about 0.010 and about 0.015 inches from transition zone 80. Thus, flap 82 will be cut off by the spinning of impeller blades 32 and 34. In this manner, the flap 82 will not become large enough to break off into an embolism and pass into the aorta.

The process of cutting off small segments of the biologic lining 79 is a continuous process to the extent that growth of the biologic lining is a continuous process. Because of the high rotational speed of the spinning pump rotor 26, any amount of growth of biologic lining into the sweep of the leading edge 84 will be almost instantaneously cut off. As a consequence, the size of the small cut-off growth of biologic lining should be in the cellular range to reduce the likelihood of embolism.

Although there are other transition zones, they are oriented to transition from an upstream smooth surface to the downstream textured surface. Thus, the extent of the formation and adherence of a biologic lining on the smooth surfaces should be minimal because of the direction of blood flow. Namely, the growth of a biologic lining in an upstream direction, against the flow of blood, should be negligible. Thus, there is a lesser need to have a mechanism to cut off biologic lining at that end.

Figure 3:
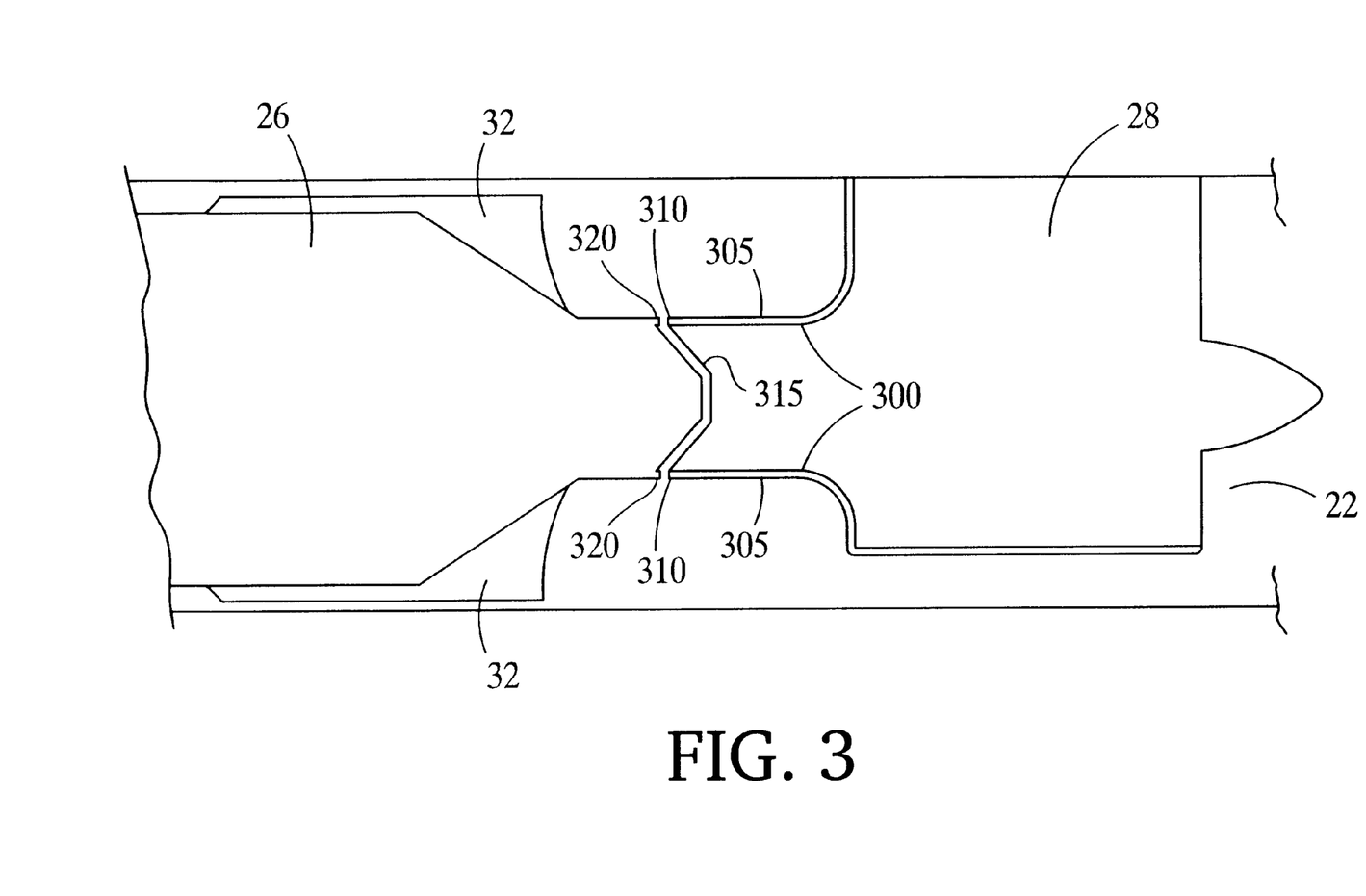
FIG. 3 is a cross-sectional view of a transition zone between a textured surface on a bearing housing and a smooth surface of the rotor of the axial flow pump of FIG. 1.

Referring to FIG. 3, inflow bearing block 28 may have a textured surface 300 that encourages or promotes the formation and adherence of a biologic lining 305, and a smooth surface 315 adjacent to the upstream end of rotor 26. As biologic lining 305 proliferates, it will form a flap 310 of tissue adjacent to the smooth bearing block surface 315. The flap 310 is unlikely to adhere, or adhere strongly, to the smooth surface 315 of bearing block 28. To prevent the flap 310 from becoming large enough to break loose and cause a serious thromboembolic complication, rotor 26 includes a pair of vanes 320 that project perpendicularly from the rotor and function as a cutting edge to cut off a segment of the flap 310 proliferating into the sweep of vanes 320. The distance between vanes 320 and bearing block 28 is approximately 0.020 inches. If tighter tolerances of the components can be achieved, the distance may be between about 0.010 and about 0.015 inches. Again, any amount of growth of biologic lining into the sweep of the vanes 320 will be almost instantaneously cut off. As a consequence, the size of the small cut-off segments typically will be in the cellular range, which is small enough to not cause thromboembolic complications.

Although the vanes are described above as projecting perpendicularly from the rotor, they may project from the rotor in a variety of configurations. For example, the vanes may be angled with respect to the rotor and spiral around the rotor so that they contribute to the pumping of the blood.

Figure 4A:
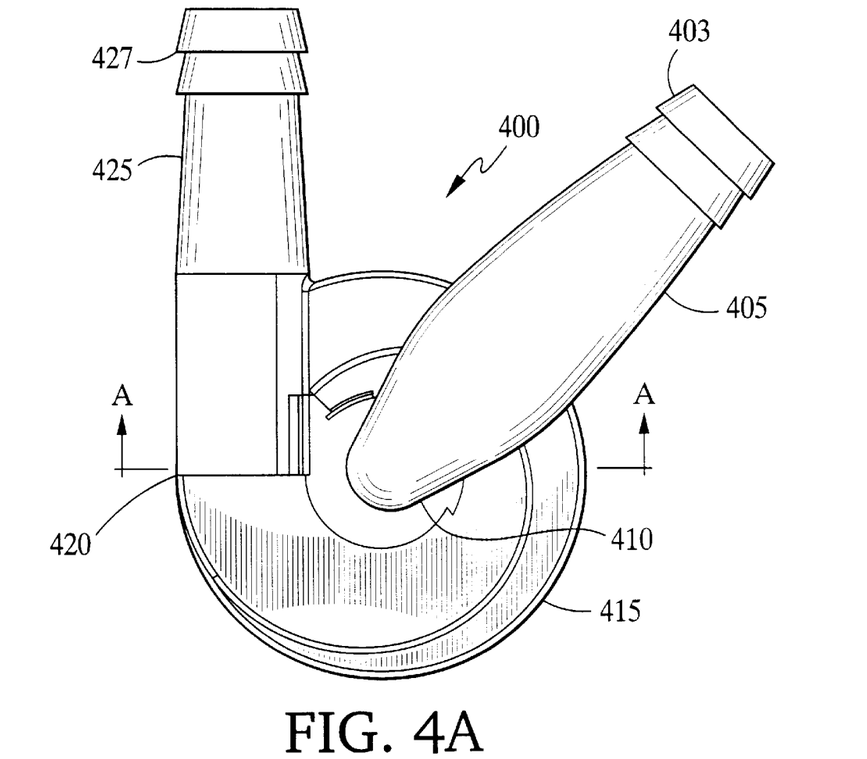
FIG. 4A is a top view of a centrifugal blood pump.
Figure 4B:
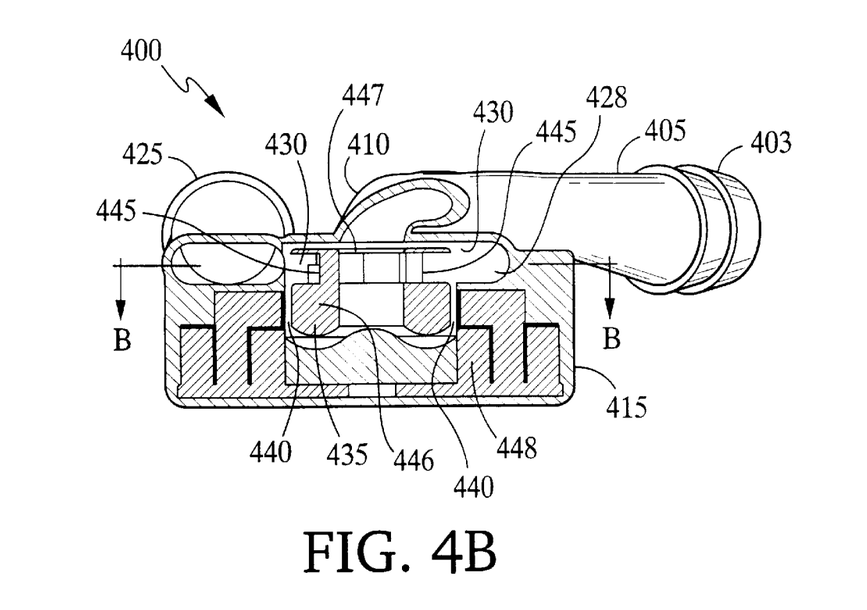
FIG. 4B is a cross-sectional side view of the centrifugal blood pump shown in FIG. 4A taken along line A—A of FIG. 4A.
Figure 4C:
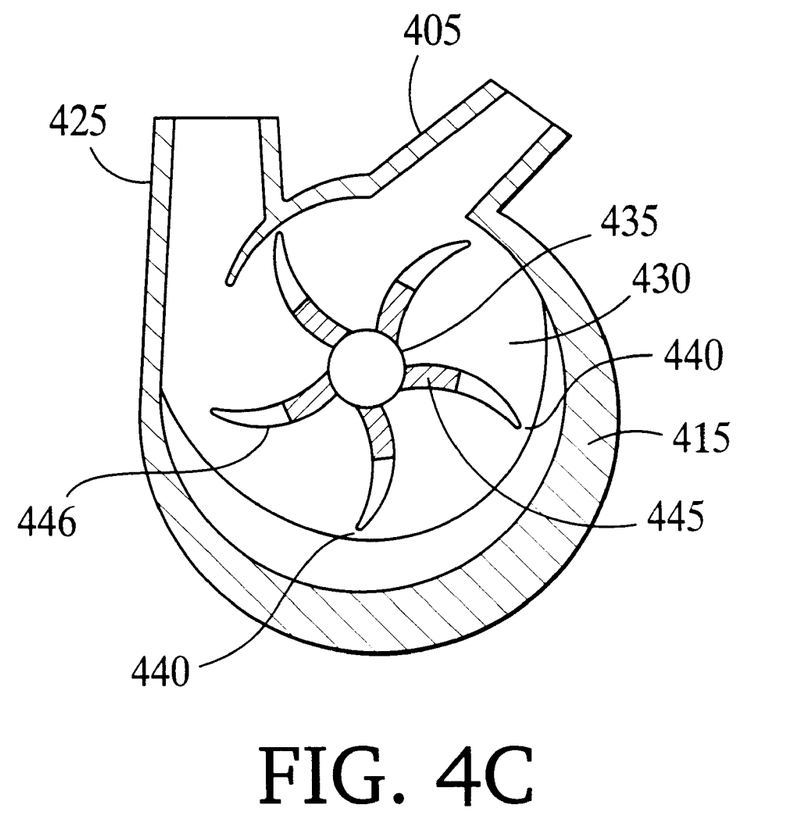
FIG. 4C is a cross-sectional top view of the centrifugal blood pump shown in FIG. 4B taken along line B—B of FIG. 4B.

In another embodiment of the textured blood contacting surface, the textured surface may by implemented in a centrifugal pump. Referring to FIGS. 4A–C, a centrifugal pump 400 includes an inflow adaptor 403, an inflow cannula 405, an inflow elbow 410, a pump body 415, an outflow elbow 420, an outflow cannula 425, and an outflow adaptor 427. Pump body 415 includes a pump housing 430, a collector region 428 of pump housing 430, a rotor 435, a narrow channel 440 defined by rotor 435 and pump body 415, and impeller blades 445. Collector region 428 collects blood being pumped by impeller blades 445 and has a configuration that directs the blood into outflow cannula 425. In addition to blades 445, rotor 435 includes a magnet base 446 and a shroud 447. Magnet base 446 is turned by an electromagnetic field created by a stator 448.

In the embodiment shown in FIGS. 4A–C, pump 400 can be attached to conventional tubing at adaptors 403 and 427 to connect it between the left ventricle and aorta to provide ventricular assistance. In another embodiment, pump 400 may be implemented using various components of pump 10 modified to function with pump 400. For example, pump 400 may be modified to incorporate inflow cannula adaptor 40, inflow cannula elbow 43, inflow cannula apical tube 45, outflow cannula elbow 49, and outflow graft 52. The modifications required are not complex and are well-known in the art.

Figure 5:
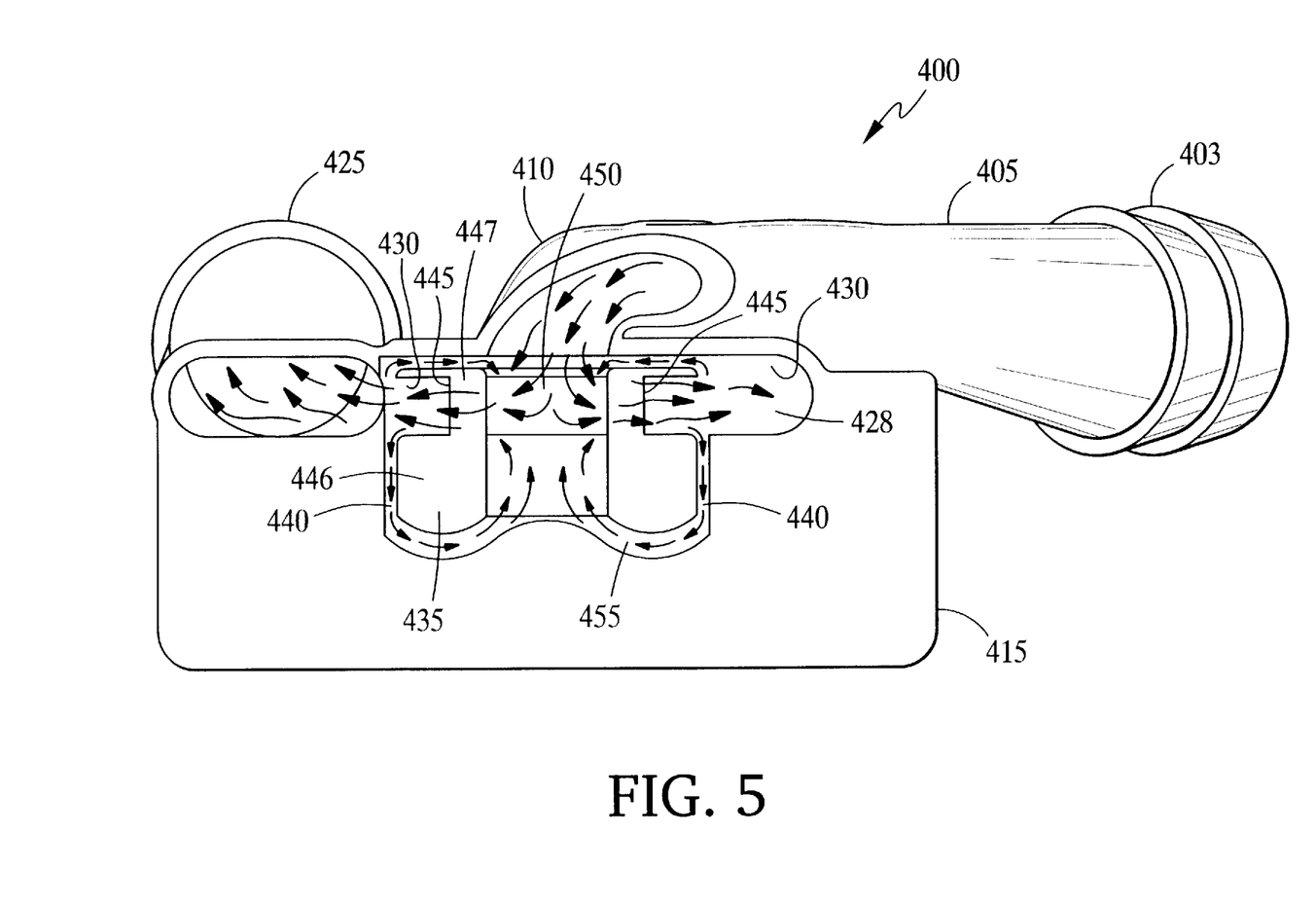
FIG. 5 is a cross-sectional side view of the centrifugal blood pump shown in FIG. 43 showing the flow pattern of blood in the pump.

Referring to FIG. 5, blood flowing in the pump 400 (represented by arrows) enters the inflow cannula 405 from the left ventricle (not shown) and passes through inflow elbow 410 into an opening 450 of shroud 447. In opening 450, the blood is swept through housing 430 by the movement of impeller blades 445 as they spin within housing 430. The blood circulates through the various regions of housing 430, namely, narrow channel 440, a space 455 of housing 430 defined between rotor 435 and the lower portion of pump body 415, and collector 428. The blood passes out of housing 430 into outflow elbow 420 and then through outflow cannula 425 into the aorta.

Figure 6:
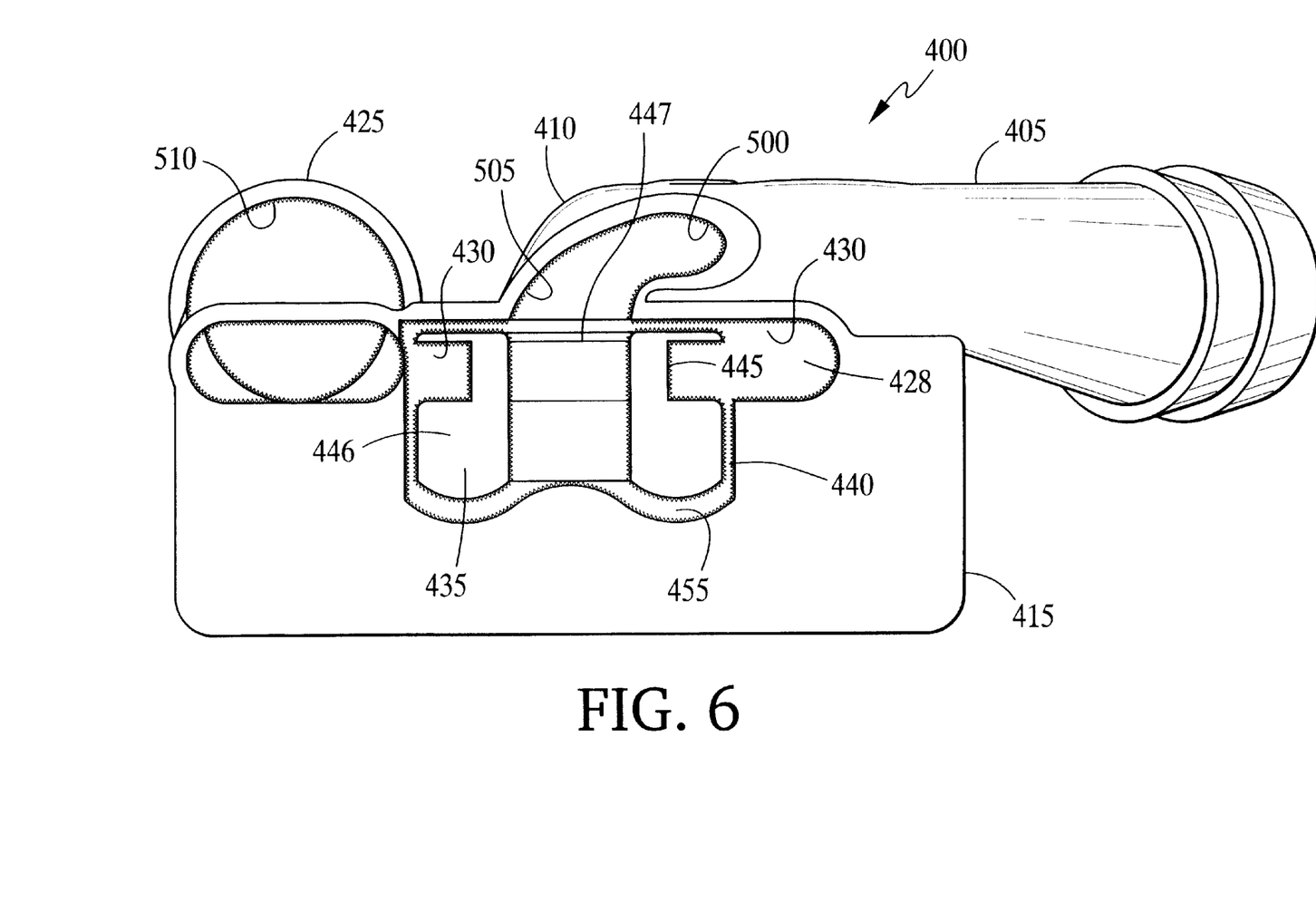
FIG. 6 is a cross-sectional side view of the centrifugal blood pump shown in FIG. 43 showing the majority of the surfaces to be textured.
Figure 7:
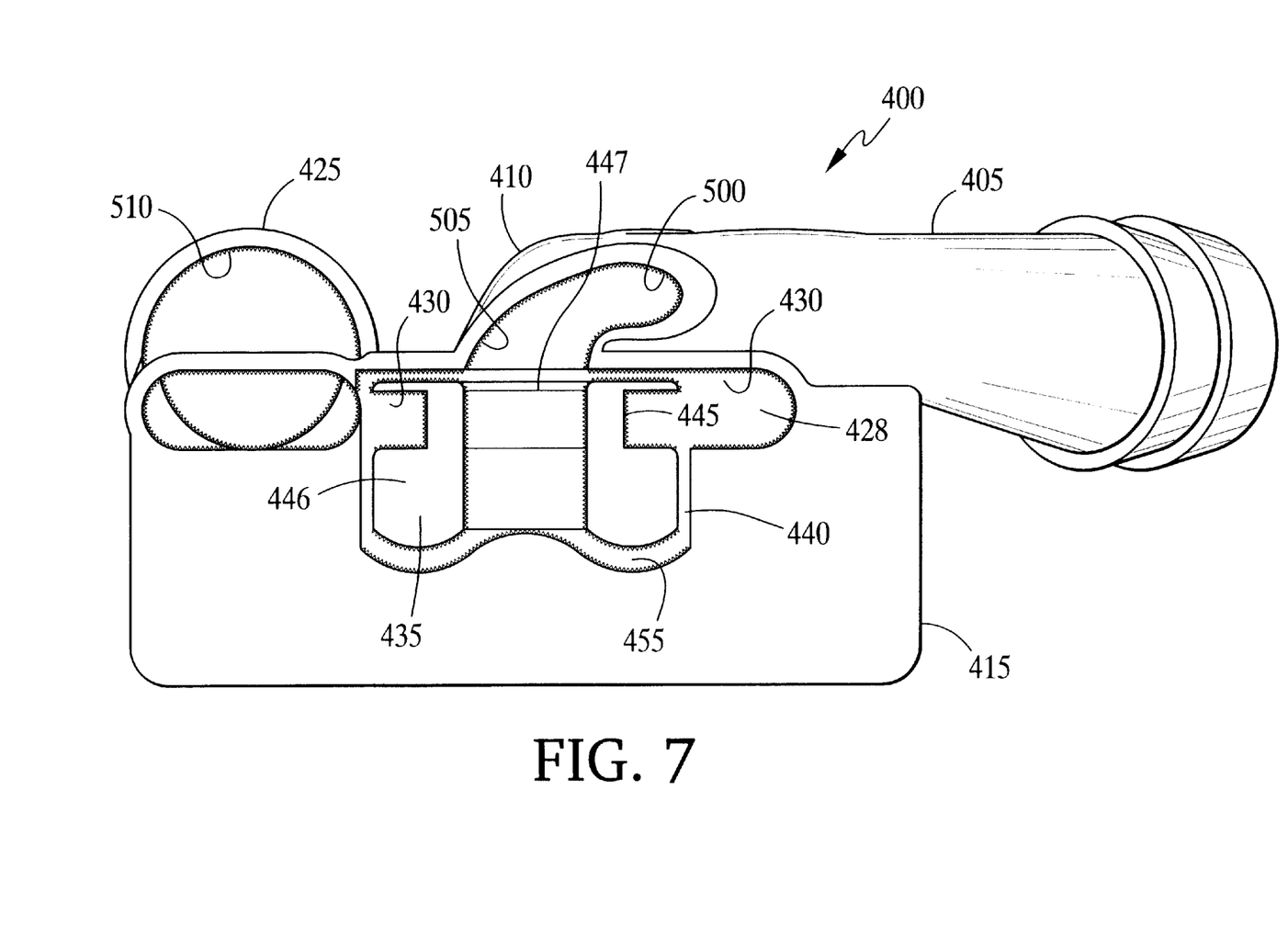
FIG. 7 is a cross-sectional side view of the centrifugal blood pump shown in FIG. 6 showing the surfaces defining the narrow channels not being textured.

Referring to FIG. 6, the pump 400 may have textured blood contacting surfaces. For example, an inside surface 500 of inflow cannula 405 and an inside surface 505 of inflow elbow 410 are textured to promote the formation and adherence of a biologic lining. Also having textured blood contacting surfaces are pump housing 430, rotor 435 (including shroud 447, impeller blades 445, and magnet base 446), narrow channels 440, an inside surface (not shown) of outflow elbow 420, and an inside surface 510 of outflow cannula 425.

Figure 8:
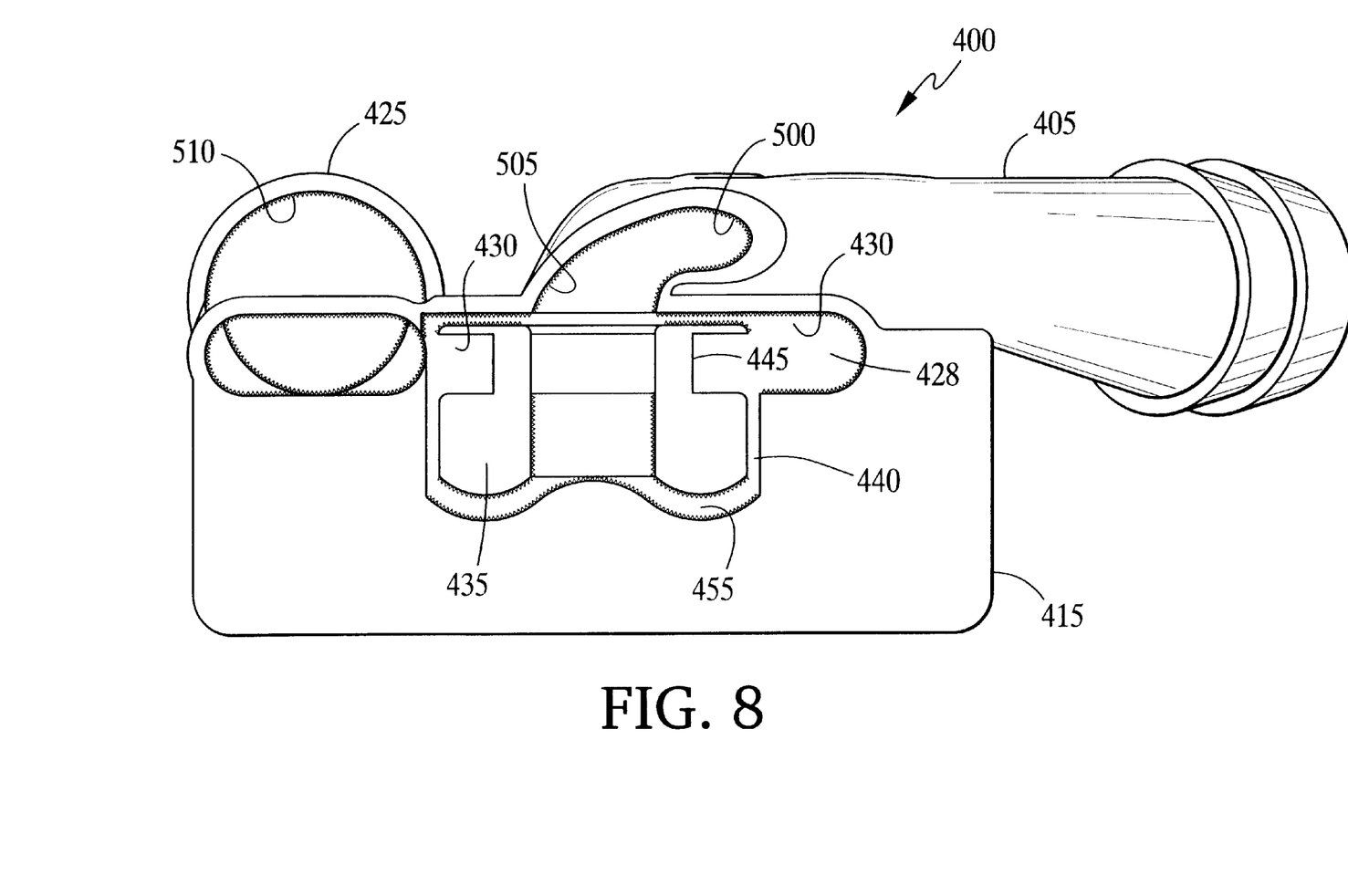
FIG. 8 is a cross-sectional side view of the centrifugal blood pump shown in FIG. 7 showing the impeller blades also not being textured.
Figure 9:
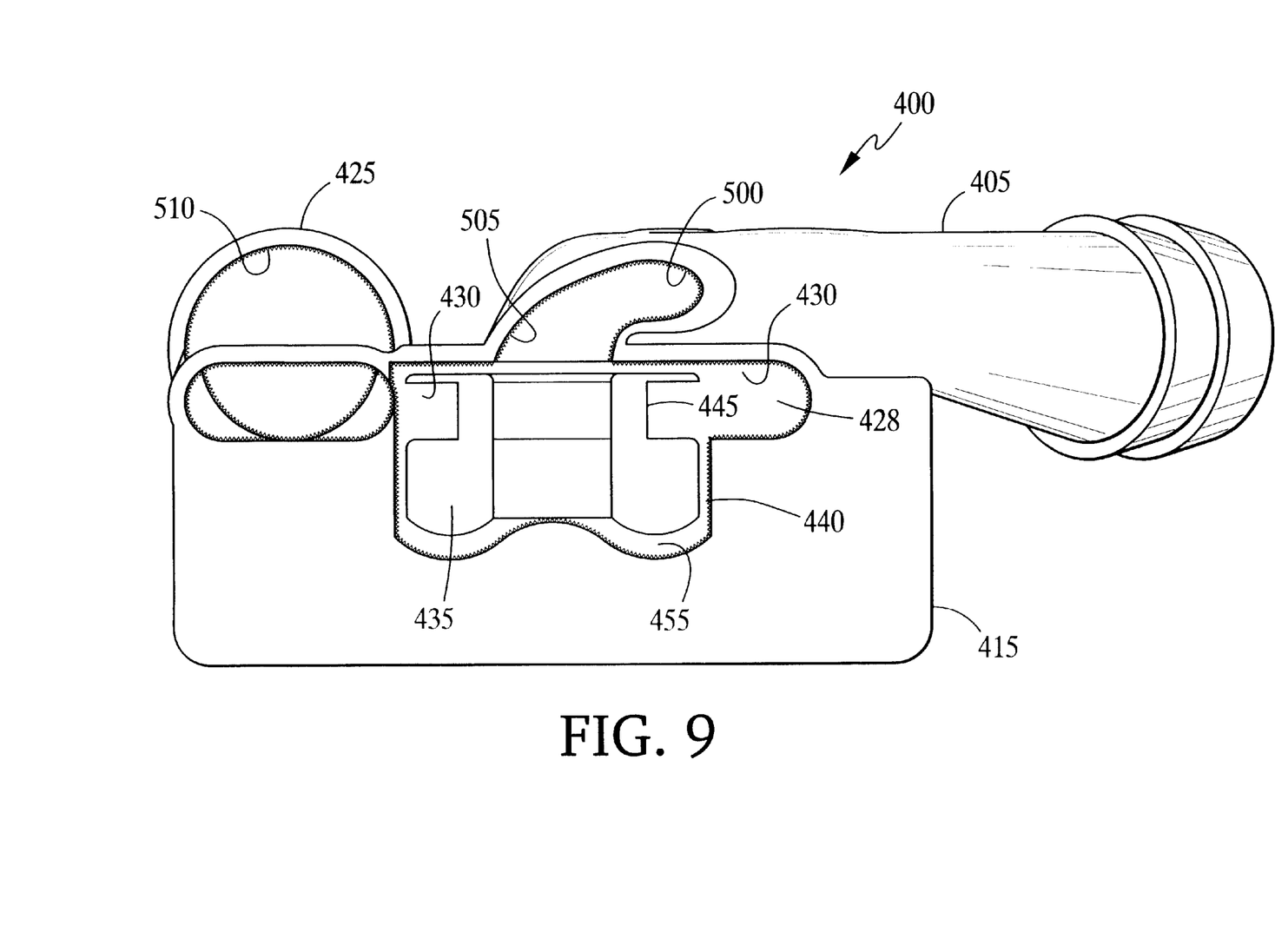
FIG. 9 is a cross-sectional side view of the centrifugal blood pump shown in FIG. 8 showing the entire rotor not being textured.
Figure 10:
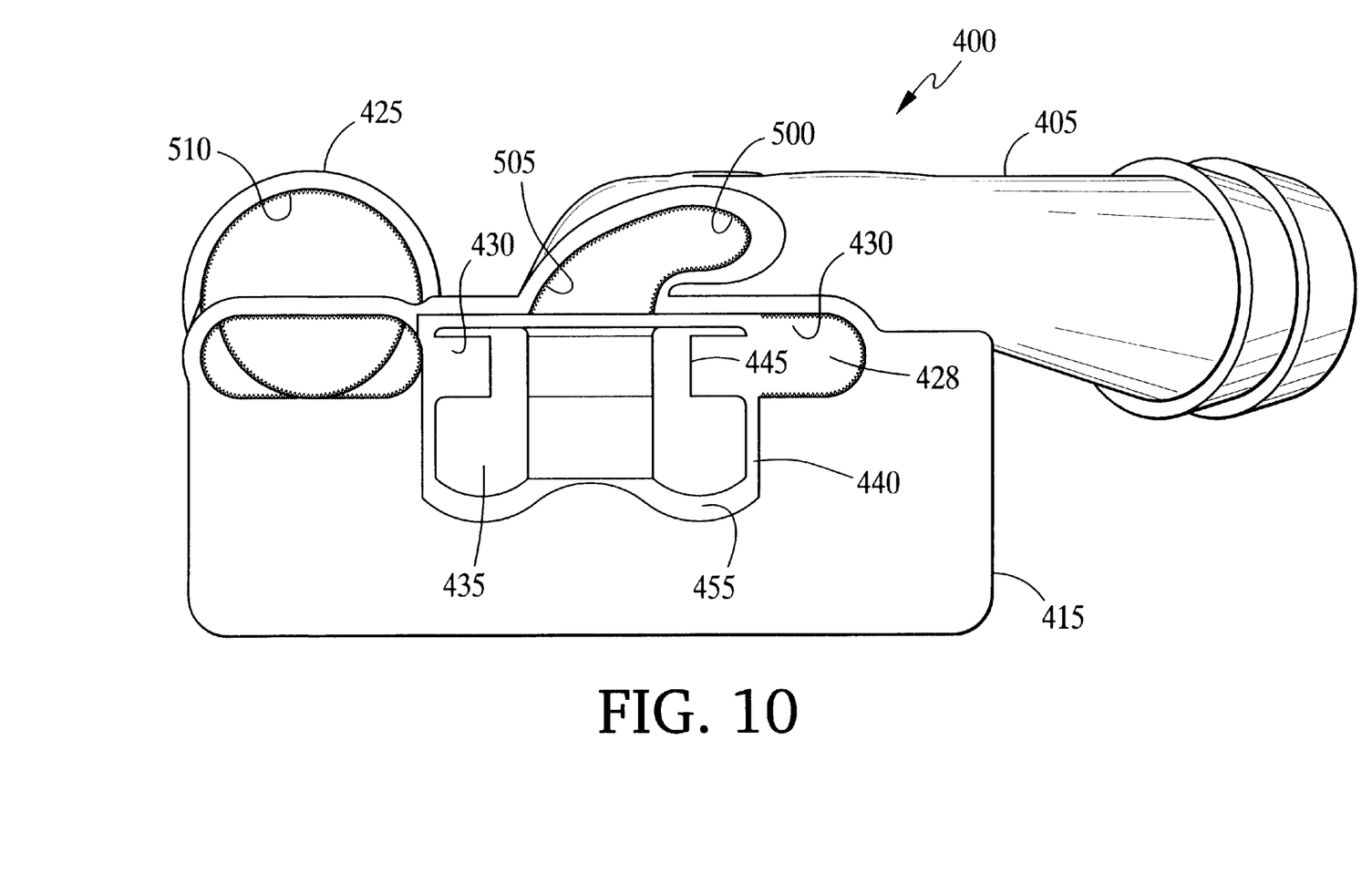
FIG. 10 is a cross-sectional side view of the centrifugal blood pump shown in FIG. 9 showing the pump housing, except for the collector region, not being textured.

Referring to FIGS. 7–10, various surfaces of the pump 400 may be textured and others left smooth. For example, in FIG. 7, all of the surfaces shown as textured in FIG. 6 are textured except for the surface of rotor 435 and body 415 defining the narrow channel 440. In FIG. 8, the impeller blades 445 also are not textured. In FIG. 9, the entire rotor 435 also is not textured. In FIG. 10, only the surfaces associated with inflow cannula 405, collector region 428 of pump housing 430, and outflow cannula 425 are textured.

In the implementations illustrated in FIGS. 6–10, a biologic lining growing into the sweep of rotor 435 from a textured/smooth surface transition will be cut off by the movement of the rotor. The cutting action will prevent the formation of a large embolism resulting from the biologic lining breaking off at the transition zone. For example, a biologic lining growing into narrow channel 440 may be cut by rotor 435. To ensure that the segments of the biologic lining cut by rotor 435 are sufficiently small to avoid thromboembolic complications, the width of narrow channel 440 is approximately 0.020 inches. Narrow channel 440 may be less if tighter tolerances on the components can be achieved.

In general, the materials of the axial flow or centrifugal pump may be selected from a wide variety of blood compatible materials, such as, for example, polymers, ceramics, titanium, and cobalt-based alloys. The transition from a textured surface to a smooth surface may be well delineated or may be gradual. A cutting edge must be positioned in a transition zone to cut off a segment of a biologic lining as it grows into the sweep of the cutting edge. The cutting edge may be placed closer to the smooth surface in some applications and closer to the textured surface in other applications. One of the factors to consider in positioning the cutting edge is the size of the flap that must be formed before it enters the sweep of the cutting edge.

Other implementations are within the scope of the following claims. For example, the rotor may have bearings to maintain the position of the rotor relative to the bearing housings. The rotor instead may be magnetically levitated (i.e., a bearingless rotor) so that the position of the rotor is maintained in the pump by means of magnetic forces.

What is claimed is:

1. A blood pump comprising:
   a blood flow channel having a textured surface and a smooth surface adjacent to the textured surface; and
   a rotor disposed within the blood flow channel, wherein the rotor includes an impeller blade that defines a sweep when the rotor turns and at least a portion of the impeller blade is configured to cut off a portion of a biologic lining as it grows from the textured surface into the sweep of the impeller blade.

2. The blood pump of claim 1, wherein the impeller blade includes a leading edge and the leading edge is positioned adjacent to the smooth surface at a distance less than about 0.020 inches from the textured surface.

3. The blood pump of claim 2, wherein the distance between the leading edge and the textured surface is between about 0.010 inches and about 0.015 inches.

4. The blood pump of claim 1, further comprising:
   a bearing mounted to the rotor;
   an inlet bearing block disposed in the blood flow channel, wherein the inlet bearing block is configured to retain the bearing; and
   at least one vane mounted to the bearing and defining a sweep of the vane when the rotor turns, wherein the inlet bearing block has a textured surface configured to encourage the formation of a biologic lining and the vane is configured to cut off a portion of the biologic lining growing from the textured surface of the inlet bearing block into the sweep of the vanes.

5. The blood pump of claim 4, wherein the distance between the vane and the inlet bearing block is less than about 0.020 inches.

6. The blood pump of claim 5, wherein the distance between the vane and the inlet bearing block is between about 0.010 inches and 0.015 inches.

7. The blood pump of claim 1, wherein the rotor is disposed within the blood flow channel adjacent to the smooth surface.

8. The blood pump of claim 1, wherein the blood pump is a rotary flow pump.

9. A method for cutting a biologic lining on a blood contacting surface, comprising:
   providing a blood pump comprising a blood flow channel having a textured surface and an adjacent smooth surface; and
   positioning a rotor within the blood flow channel, wherein the rotor has an impeller blade that defines a sweep when the rotor turns and the impeller blade is configured to cut off a portion of a biologic lining as it grows from the textured surface into the sweep of the impeller blade.

10. The method of claim 9, wherein the impeller blade includes a leading edge, and the leading edge is positioned adjacent to the smooth surface at a distance less than about 0.020 inches from the textured surface.

11. The method of claim 10, wherein the distance between the leading edge and the textured surface is between about 0.010 inches and about 0.015 inches.

12. The method of claim 9, further comprising:
   mounting a bearing to the rotor;
   disposing an inlet bearing block in the blood flow channel, wherein the bearing block is configured to retain the bearing; and
   mounting at least one vane to the bearing, wherein the vane defines a sweep when the rotor turns, and wherein the inlet bearing block has a textured surface configured to encourage the formation of a biologic lining and the vane is configured to cut off a portion of the biologic lining growing from the textured surface of the inlet bearing block into the sweep of the vanes.

13. The method of claim 12, wherein the distance between the vane and the inlet bearing block is less than about 0.020 inches.

14. The method of claim 13, wherein the distance between the vane and the inlet bearing block is between about 0.010 inches and about 0.015 inches.

15. The method of claim 9, wherein the rotor is disposed within the blood flow channel adjacent to the smooth surface.

16. A blood pump comprising:
   a pumping chamber having a collector region including a textured blood contacting surface;
   a pump housing; and
   a rotor disposed within the pump housing, wherein the pump housing and the rotor define a channel, and the rotor is configured to cut a biologic lining growing into the sweep of the rotor.

17. The blood pump of claim 16, wherein the channel has a textured blood contacting surface.

18. The blood pump of claim 17, wherein the width of the channel is less than about 0.020 inches.

19. The blood pump of claim 16, wherein the rotor has a textured blood contacting surface.

20. The blood pump of claim 16, wherein the pumping chamber has a textured blood contacting surface.

21. The blood pump of claim 16, wherein the blood pump is a centrifugal pump.

22. An embolism-resistant device comprising: a textured blood contacting surface on which a biologic lining can grow;
   a smooth blood contacting surface adjacent to the textured surface; and
   a cutting mechanism that cuts a portion of the biologic lining as the biologic lining grows from the textured surface onto the smooth surface.

23. The device of claim 22, wherein the cutting means is positioned less than about 0.020 inches from the textured surface.

24. The device of claim 23, wherein the cutting mechanism is positioned between about 0.010 and about 0.015 inches from the textured surface.

25. The device of claim 22, wherein the device comprises a blood pump.

26. A blood pump comprising:
   a blood flow path having a region that is susceptible to tissue growth;
   a rotor disposed within the blood flow path; and
   a stator that rotates the rotor within the blood flow path, wherein the rotor drives a cutting mechanism that cuts the tissue growing within the blood flow path, thereby reducing the risks of embolism.

* * * * *